US011413065B2

(12) United States Patent
Pilletere et al.

(10) Patent No.: US 11,413,065 B2
(45) Date of Patent: Aug. 16, 2022

(54) SEAL ASSEMBLIES FOR SURGICAL ACCESS ASSEMBLIES

(71) Applicant: Covidien LP, Mansfield, MA (US)

(72) Inventors: Roy Pilletere, North Haven, CT (US); Matthew Dinino, Newington, CT (US); Garrett Ebersole, Hamden, CT (US); Kevin Desjardin, Cheshire, CT (US); Justin Thomas, New Haven, CT (US); Jacob Baril, Norwalk, CT (US); Nicolette LaPierre, Windsor Locks, CT (US); Eric Brown, Haddam, CT (US)

(73) Assignee: Covidien LP, Mansfield, MA (US)

( * ) Notice: Subject to any disclaimer, the term of this patent is extended or adjusted under 35 U.S.C. 154(b) by 285 days.

(21) Appl. No.: 16/455,838

(22) Filed: Jun. 28, 2019

(65) Prior Publication Data
US 2020/0405349 A1      Dec. 31, 2020

(51) Int. Cl.
| A61B 17/34 | (2006.01) |
| A61B 17/02 | (2006.01) |
| A61M 39/06 | (2006.01) |

(52) U.S. Cl.
CPC ...... *A61B 17/3421* (2013.01); *A61B 17/0218* (2013.01); *A61B 17/3462* (2013.01); *A61M 39/0606* (2013.01); *A61B 17/3498* (2013.01); *A61B 2017/3419* (2013.01); *A61B 2017/3464* (2013.01); *A61B 2017/3466* (2013.01); *A61M 2039/0626* (2013.01)

(58) Field of Classification Search
CPC ............ A61B 17/3421; A61B 17/0218; A61B 17/3462; A61B 17/3498; A61B 2017/3419; A61B 2017/3464; A61B 2017/3466; A61M 39/0606; A61M 2039/0626; A61M 2039/0666
See application file for complete search history.

(56) References Cited

U.S. PATENT DOCUMENTS

| 3,402,710 A | 9/1968 | Paleschuck |
| 3,495,586 A | 2/1970 | Regenbogen |
(Continued)

FOREIGN PATENT DOCUMENTS

| CA | 2702419 A1 | 11/2010 |
| EP | 0226026 A2 | 6/1987 |
(Continued)

OTHER PUBLICATIONS

European Search Report dated Sep. 11, 2020, corresponding to counterpart European Application No. 20182478.6; 11 pages.

*Primary Examiner* — Theodore J Stigell
(74) *Attorney, Agent, or Firm* — Carter, DeLuca & Farrell LLP

(57) ABSTRACT

Surgical access assemblies include an instrument valve housing and a valve assembly disposed within the cavity of the instrument valve housing. The valve assembly includes a guard assembly, a seal assembly disposed adjacent to the guard assembly, and a centering mechanism for maintaining the seal assembly and guard assembly centered within a cavity of the instrument valve. The seal assembly includes a multi-petal seal member and upper and lower support members. The upper and lower support members sandwich the multi-petal seal member therebetween to reduce and/or eliminate leaks through the multi-petal seal member.

19 Claims, 9 Drawing Sheets

(56) References Cited

U.S. PATENT DOCUMENTS

| | | |
|---|---|---|
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |

(56) References Cited

U.S. PATENT DOCUMENTS

| | | |
|---|---|---|
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,913,697 B2 | 3/2011 | Nguyen et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,092,430 B2 | 1/2012 | Richard et al. |
| 8,105,234 B2 | 1/2012 | Ewers et al. |
| 8,109,873 B2 | 2/2012 | Albrecht et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 8,241,209 B2 | 8/2012 | Shelton, IV et al. |
| 8,262,568 B2 | 9/2012 | Albrecht et al. |
| 8,323,184 B2 | 12/2012 | Spiegal et al. |
| 8,335,783 B2 | 12/2012 | Milby |
| 8,343,047 B2 | 1/2013 | Albrecht et al. |
| 8,353,824 B2 | 1/2013 | Shelton, IV et al. |
| 8,403,889 B2 | 3/2013 | Richard |

(56) References Cited

U.S. PATENT DOCUMENTS

| | | |
|---|---|---|
| 8,480,683 B2 | 7/2013 | Fowler et al. |
| 8,574,153 B2 | 11/2013 | Richard |
| 8,585,632 B2 | 11/2013 | Okoniewski |
| 10,568,660 B2 | 2/2020 | Zhou |
| 10,653,449 B2 | 5/2020 | Main et al. |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0187376 A1 | 10/2003 | Rambo |
| 2003/0233115 A1 | 12/2003 | Eversull et al. |
| 2003/0236549 A1 | 12/2003 | Bonadio et al. |
| 2004/0059297 A1 | 3/2004 | Racenet |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0230161 A1* | 11/2004 | Zeiner ............... A61B 17/3498 604/167.06 |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0119525 A1 | 6/2005 | Takemoto |
| 2005/0137459 A1 | 6/2005 | Chin et al. |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0209608 A1 | 9/2005 | O'Heeron |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0211992 A1* | 9/2006 | Prosek ............... A61B 17/3421 604/167.06 |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0146882 A1* | 6/2008 | Cropper ............ A61B 17/3423 600/206 |
| 2008/0161826 A1 | 7/2008 | Guiraudon |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0228094 A1 | 9/2010 | Ortiz et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251560 A1 | 10/2011 | Albrecht et al. |
| 2011/0313250 A1 | 12/2011 | Kleyman |
| 2012/0059640 A1 | 3/2012 | Roy et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |

(56) References Cited

U.S. PATENT DOCUMENTS

| | | |
|---|---|---|
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2013/0225930 A1 | 8/2013 | Smith |
| 2013/0225931 A1 | 8/2013 | Cruz et al. |
| 2013/0245373 A1 | 9/2013 | Okoniewski |
| 2013/0274559 A1 | 10/2013 | Fowler et al. |
| 2013/0310651 A1 | 11/2013 | Alfieri |
| 2014/0018632 A1 | 1/2014 | Kleyman |
| 2015/0223833 A1 | 8/2015 | Coffeen et al. |
| 2019/0059938 A1 | 2/2019 | Holsten |
| 2019/0059944 A1 | 2/2019 | Holsten |
| 2019/0142460 A1* | 5/2019 | Zhu .................. A61B 17/3462 604/167.01 |
| 2020/0397474 A1* | 12/2020 | Pilletere ............ A61B 17/3498 |

FOREIGN PATENT DOCUMENTS

| | | |
|---|---|---|
| EP | 0538060 A1 | 4/1993 |
| EP | 0568383 A1 | 11/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2010072 A1 | 1/2009 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| EP | 3242615 * | 11/2017 |
| EP | 3242615 A1 | 11/2017 |
| GB | 2469083 | 4/2009 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2012131746 A1 | 10/2012 |
| WO | WO-2012/131746 * | 10/2012 |
| WO | 2014052532 A1 | 4/2014 |
| WO | 2014116889 A1 | 7/2014 |

\* cited by examiner

SEAL ASSEMBLIES FOR SURGICAL ACCESS ASSEMBLIES

FIELD

The present disclosure relates to surgical access assemblies for minimally invasive surgery, including seals. More particularly, the present disclosure relates to seals for surgical access assemblies.

BACKGROUND

In order to facilitate minimally invasive surgery, a working space is created at a surgical site. An insufflation fluid, typically $CO_2$, is introduced into the abdomen of the patient to create an inflated state called a pneumoperitoneum. Surgical access assemblies are utilized to allow the introduction of surgical instrumentation and endoscopes (or other visualization tools). These surgical access assemblies maintain the pressure for the pneumoperitoneum, as they have one or more seals that adapt to the surgical instrumentation. Typically, a "zero-seal" in the surgical access assembly seals the surgical access assembly in the absence of a surgical instrument in the surgical access assembly, and an instrument seal seals around a surgical instrument that has been inserted through the surgical access assembly.

The breadth of surgical instrumentation on the market today requires a robust seal capable adjusting to multiple sizes and withstanding multiple insertions of surgical instrumentation. Some of the instrumentation can include sharp edges that can tear or otherwise damage seals. Therefore, it would be beneficial to have a surgical access assembly with improved seal durability.

SUMMARY

A surgical access assembly with improved seal durability is provided. The surgical access assembly includes an instrument valve housing including upper, lower, and inner housing sections and defining a cavity, and a valve assembly disposed within the cavity of the instrument valve housing. The valve assembly includes a guard assembly including a plurality of guard sections, a seal assembly disposed adjacent to the guard assembly, and a centering mechanism for maintaining the seal assembly and guard assembly centered within the cavity of the instrument valve. The seal assembly includes a plurality of seal sections and upper and lower support members. The plurality of seal sections are movable from an unfolded configuration to folded configuration in which the seal assembly forms an octagonal member defining an opening to facilitate sealed passage of a surgical instrument. The upper and lower support members are received on respective proximal and distal sides of the plurality of seal sections and compressed about the plurality of seal sections to sandwich the plurality of seal sections therebetween.

In embodiments, the upper and lower support members define an opening from about 0.30" to about 0.45". The upper and lower support members may measure from about 0.006" to about 0.015" in thickness. The plurality of seal sections may be formed of polyisoprene or liquid silicone rubber. Each seal section of the plurality of seal sections may be connected to an adjacent seal section of the plurality of seal sections by a connector portion. The connector portions may include living hinges. The upper support member may be connected to a seal section of the plurality of seal sections by a connector portion and the lower support member may be connected to another seal section of the plurality of seal sections by another connector portion.

In some embodiments, an inner edge of each seal section of the plurality of seal sections may define a V-shape. The V-shape may include an angle from about one hundred eighty degrees to about two hundred seventy-five degrees. The plurality of seal sections may include first, second, third, and fourth seal sections, each of the first, second, third, and fourth seal sections overlapping the adjacent second, third, fourth, and first seal sections.

The surgical access assembly may further include a retainer assembly including upper and lower retainer members. At least one of the upper or lower retainer members may include a plurality of pins receivable through the guard assembly and the seal assembly for retaining the guard and seal assemblies relative to each other. The centering mechanism may include a bellows. The upper and lower support members may include a hexagonal shape. The upper and lower support members may include an octagonal shape.

A valve assembly including a seal assembly with improved durability is provided. The valve assembly includes a guard assembly including a plurality of guard sections, a seal assembly disposed adjacent to the guard assembly, and a centering mechanism for maintaining the seal assembly and guard assembly centered within a cavity of an instrument valve. The seal assembly includes a plurality of seal sections and upper and lower support members. The plurality of seal sections are movable from an unfolded configuration to folded configuration in which the seal assembly forms an octagonal member defining an opening to facilitate sealed passage of a surgical instrument therethrough. The upper and lower support members are disposed on respective proximal and distal sides of the plurality of seal sections and compressed about the plurality of seal sections to sandwich the plurality of seal sections therebetween.

In embodiments, the valve assembly further includes a retainer assembly having upper and lower retainer members. At least one of the upper and lower retainer members may include a plurality of pins receivable through the guard assembly and the seal assembly for retaining the guard and seal assemblies relative to each other. The upper support member may be connected to a seal section of the plurality of seal sections by a connector portion and the lower support member is connected to another seal section of the plurality of seal sections by another connector portion.

A seal assembly with improved durability is provided. The seal assembly includes a plurality of seal sections movable from an unfolded configuration to folded configuration in which the seal assembly forms an octagonal member defining an opening to facilitate sealed passage of a surgical instrument, an upper support member disposed proximally of the plurality of seal sections, and a lower support member disposed distally of the plurality of seal sections. The upper and lower support members are compressed about the plurality of seal sections to sandwich the plurality of seal sections therebetween.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
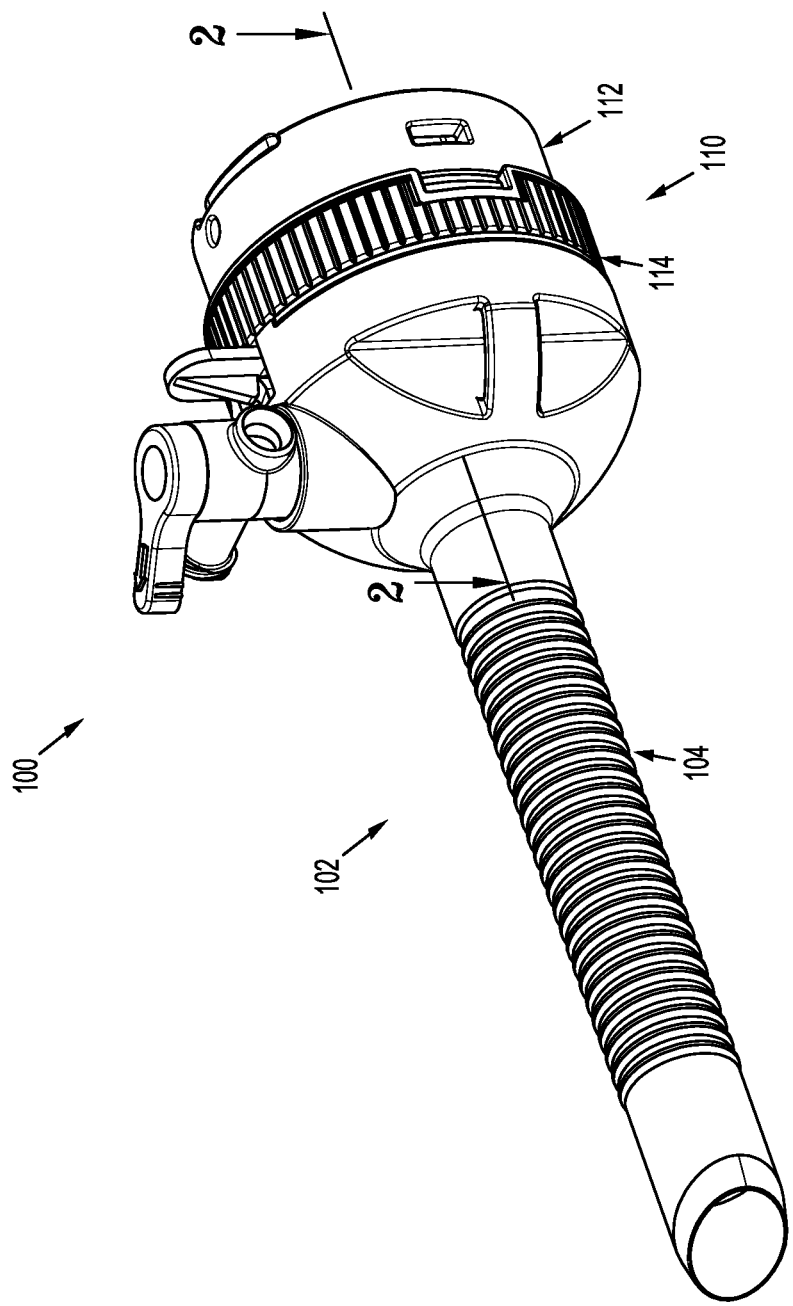
FIG. 1 is a side perspective view of an surgical access assembly according to an embodiment of the present disclosure.

Particular embodiments of the present surgical access assemblies are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Surgical access assemblies are employed during minimally invasive surgery, e.g., laparoscopic surgery, and provide for the sealed access of surgical instruments into an insufflated body cavity, such as the abdominal cavity. The surgical access assembly of the present disclosure includes an instrument valve housing mounted on a cannula tube, and an obturator (not shown) inserted through the valve housing and cannula. The obturator can have a blunt distal end, or a bladed or non-bladed penetrating distal end and can be used to incise the abdominal wall so that the surgical access assembly can be introduced into the abdomen. The handle of the obturator can engage or selectively lock onto the instrument valve housing of the surgical access assembly.

Surgical access assemblies are employed to tunnel through an anatomical structure, e.g., the abdominal wall, either by making a new passage through the structure or by passing through an existing opening through the structure. Once the trocar assembly has tunneled through the anatomical structure, the trocar obturator is removed, leaving the cannula assembly in place. The instrument valve housing of the cannula includes valves that prevent the escape of insufflation fluids from the body cavity, while also allowing surgical instruments to be inserted into the body cavity.

In various embodiments, a bladeless optical trocar obturator may be provided that permits separation of tissue planes in a surgical procedure and visualization of body tissue fibers as they are being separated, thereby permitting a controlled traversal across a body wall. In other embodiments, the trocar obturator may be bladeless without being optical, e.g., without providing contemporaneous visualization thereof through the distal tip of an obturator. The bladeless obturator may be provided for the blunt dissection of the abdominal lining during a surgical procedure.

Various trocar obturators suitable for use with the cannulas of the present disclosure are known and include, for example, bladed, bladeless, blunt, optical, non-optical. For a detailed description of the structure and function of exemplary trocar assemblies, including exemplar trocar obturators and exemplar cannulas, please refer to commonly owned PCT Publication No. WO 2016/186905 ("the '905 publication"), the content of which is hereby incorporated by reference herein in its entirety.

With initial reference now to FIG. 1, a surgical access assembly according to aspects of the present disclosure is shown generally as cannula assembly 100. The cannula assembly 100 includes a cannula 102 and an instrument valve housing 110 secured to the cannula 102. For a detailed description of an exemplary cannula assembly, please refer to the '905 publication.

Figure 2:
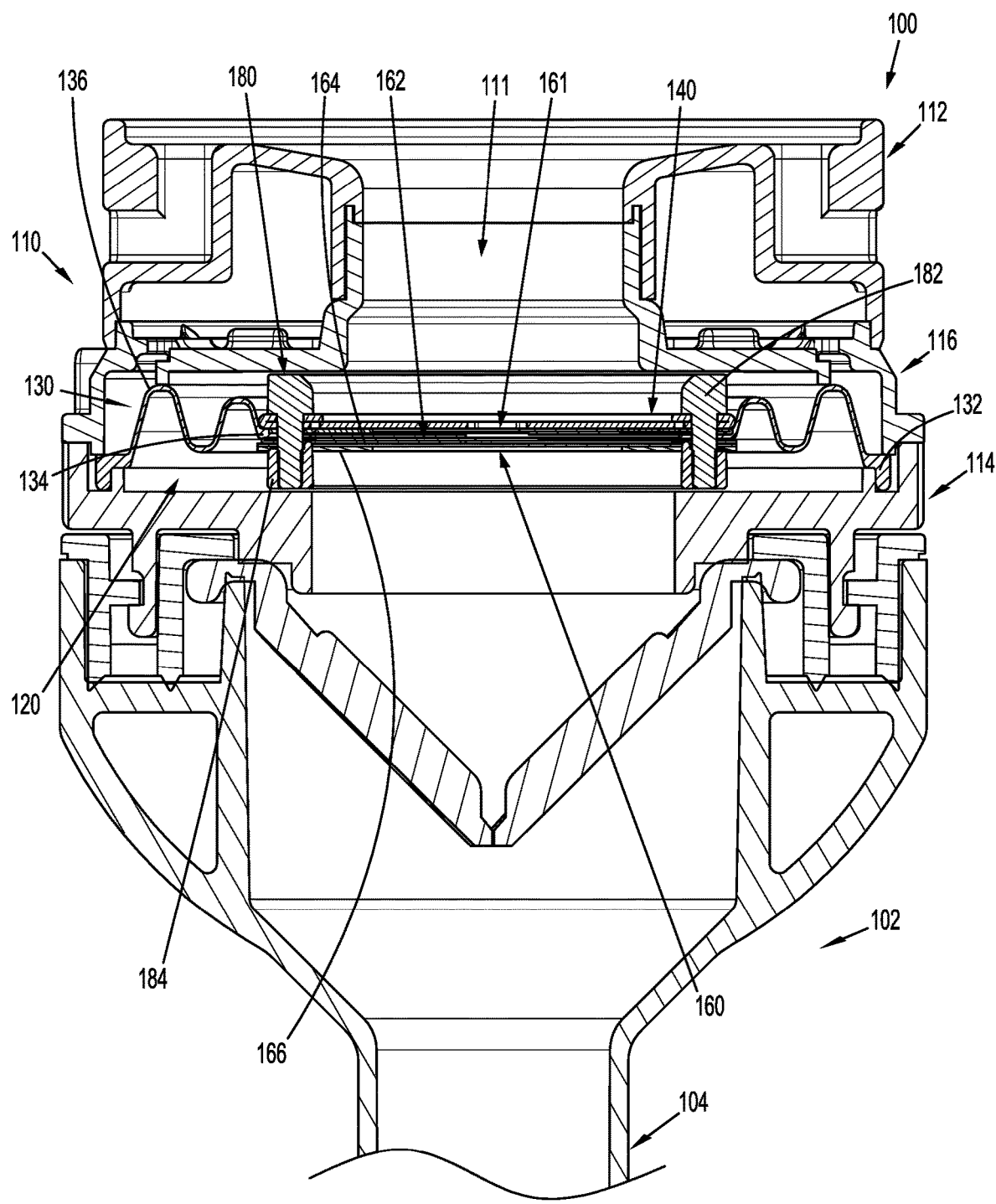
FIG. 2 a side cross-sectional view of the surgical access assembly shown in FIG. 1 taken along section line 2-2.

With reference to FIG. 2, the instrument valve housing 110 of the cannula assembly 100 includes an upper housing section 112, a lower housing section 114, and an inner housing section 116. The upper, lower, and inner housing sections 112, 114, 116 are configured to support a valve assembly 120 on a proximal end of the cannula 102. More particularly, the inner housing section 116 is secured between the upper and lower housing sections 112, 114, and the valve assembly 120 is received between the inner and lower housing sections 116, 114. The upper and lower housing sections 112, 114 of the instrument valve housing 110 may be selectively attachable to, and detachable from, the inner housing section 116. The lower housing section 114 may be releasably or permanently attached to a cannula tube 104 of the cannula assembly 102. In embodiments, either or both of the upper and lower housing sections 112, 114 of the instrument valve housing 110 may include knurls, indentations, tabs, or be otherwise configured to facilitate engagement by a clinician.

The cannula assembly 100 may also include features for the stabilization of the surgical access assembly. For example, the distal end of the cannula tube 104 may carry a balloon anchor or another expandable member that engages the abdomen from the interior side. For example, see U.S. Pat. No. 7,300,448, the entire disclosure of which is hereby incorporated by reference herein. A feature on the opposite side of the abdominal wall may be used to further stabilize the surgical access assembly, such as adhesive tabs or adjustable foam collars.

The upper, lower, and inner housing sections 112, 114, 116 of the instrument valve housing 110 define a longitudinal passage 111 for receipt of a surgical instrument (not shown). The valve assembly 120 is supported within the instrument valve housing 110 to provide sealed passage of the surgical instrument through the cannula assembly 100.

Figure 3:
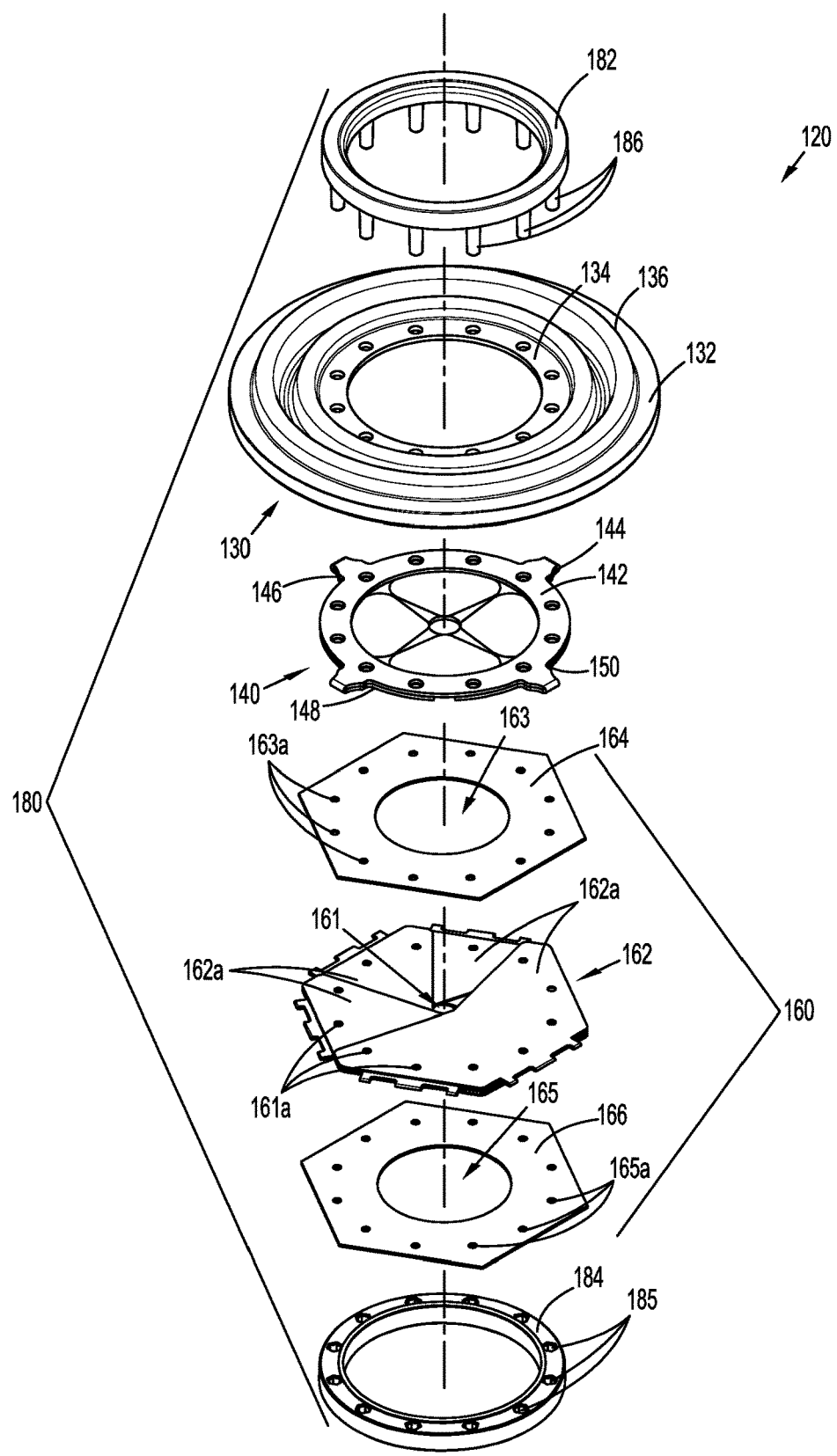
FIG. 3 is a perspective view with parts separated of the valve assembly shown in FIG. 2, including a centering mechanism, a guard assembly, a seal assembly, and a retainer assembly.
Figure 4:
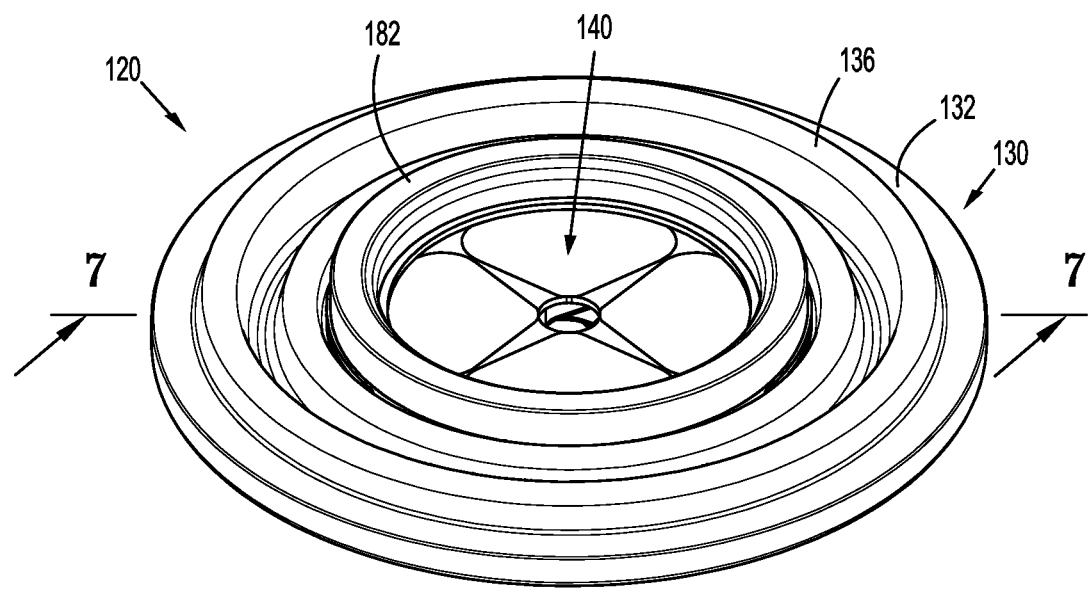
FIG. 4 is a top perspective view of the seal assembly shown in FIG. 3.
Figure 5:
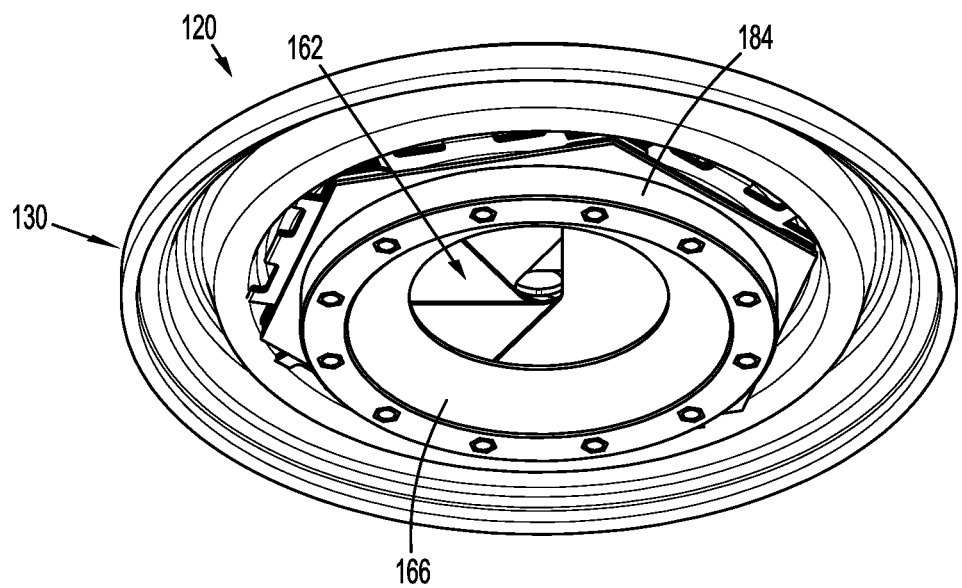
FIG. 5 is a bottom perspective view of the seal assembly shown in FIG. 3.

With particular reference to FIGS. 2 and 3, the valve assembly 120 supported in the instrument valve housing 110 (FIG. 2) includes a centering mechanism 130, a guard assembly 140, a seal assembly 160, and a retainer assembly 180. The centering mechanism 130 of the valve assembly 120 permits radial movement of the valve assembly 120 relative to the instrument valve housing 110 when a surgical instrument is received through the valve assembly 120, and otherwise maintains the valve assembly 120 in a generally centered position within the instrument valve housing 110. The guard assembly 140 protects the seal assembly 160 during insertion and withdrawal of a surgical instrument through the seal assembly 160. The seal assembly 160 provides sealed passage of the surgical instrument through the instrument valve housing 110. The retainer assembly 180 maintains the centering mechanism 130, the guard assembly 140, and the seal assembly 160 in an aligned relationship with one another.

With continued reference to FIGS. 2 and 3, as noted above, the centering mechanism 130 of the valve assembly 120 is configured to maintain the valve assembly 120 centered within the instrument valve housing 110 (FIG. 2). In embodiments, and as shown, the centering mechanism 130 includes an outer annular ring 132, an inner annular ring 134, and a bellows 136 disposed between the outer annular ring 132 and the inner annular ring 134. As shown in FIG. 2, the outer annular ring 132 is received between the inner housing section 116 and the lower housing section 114 to retain the centering mechanism 130 within the instrument valve housing 110. The inner annular ring 134 supports the seal assembly 160. For a detailed description of the structure and function of an exemplary centering mechanism, please refer to U.S. Pat. No. 6,702,787, the content of which is incorporated herein by reference in its entirety.

Although the centering mechanism 130 is shown having bellows 136, the valve assembly 120 may include alternative centering mechanisms. For example, the centering mechanism may include an annular base and a plurality of spokes extending from the base, as described in commonly owned U.S. Pat. App. Pub. No. 2015/0025477 ("the '477 publication"), the content of which is incorporated herein by reference in its entirety. It is envisioned that the centering mechanism may include multiple sets of spokes, as disclosed in the '477 publication.

Still referring to FIGS. 2 and 3, the guard assembly 140 of the valve assembly 120 includes a ring portion 142 and first, second, third, and fourth petals 144, 146, 148, 150. The guard assembly 140 may be formed from a sheet of plastic/polymeric material by stamping with a tool that forms the ring portion 142 and the petals 144, 146, 148, 150. Alternatively, the guard assembly 140 may be formed by molding or other techniques. It is envisioned that the guard assembly may include any number of petals, and the petals may include flap portions of any size or configuration. For exemplary guard assemblies, as well as other aspects of surgical access assembly, please refer to U.S. Pat. Nos. 5,895,377 and 6,569,120, the entire disclosures of which are hereby incorporated by reference herein. For detailed description of the structure and function of other exemplary guard assemblies, please refer to commonly owned U.S. patent application Ser. Nos. 16/394,043, 16/238,823, and 62/912,104, the content of which is incorporated herein by reference in its entirety.

With continued reference now to FIGS. 2 and 3, the seal assembly 160 of the valve assembly 120 is configured to provide a seal around an outer surface of a surgical instrument (not shown) passing through the instrument valve housing 110 (FIG. 2).

The seal assembly 160 includes a multi-petal or section seal member 162, and upper and lower support members 164, 166. As shown, the multi-petal seal member 162 includes a six petal or sections forming a hexagonal body and defining an opening 161. Although shown including six (6) sections, it is envisioned that the seal assembly 160 may include any suitable number of sections, such as, for example, as few as four (4) sections, or as many as eight (8) sections. By forming the opening 161 of the multi-petal seal member 162 out of multiple petals instead of as a continuous solid opening through a single seal member, the likelihood of the multi-petal seal member 162 tearing during insertion, removal, and use of a surgical instrument therethrough is greatly reduced. Although shown having overlapping wing-shaped petals 162a, it is envisioned that the aspects of the present disclosure may be modified for use with seal members having petals of alternative configurations and arrangements. An exemplary multi-petal seal member is shown and described in U.S. patent application Ser. No. 16/272,068, filed Feb. 11, 2019, the content of which is incorporated herein in its entirety.

Figure 6:
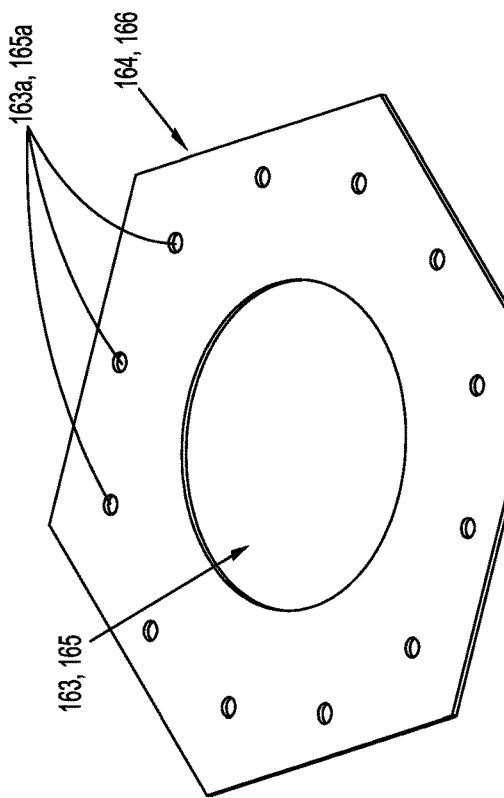
FIG. 6 is a perspective view of a support member of the seal assembly shown in FIG. 3.

With particular reference to FIG. 6, the upper and lower support members 164, 166 of the seal assembly 160 each include a hexagonal shape, corresponding to the shape of the multi-petal seal member 162, and each an opening 163, 165, respectively. Although shown as having a hexagonal body, the upper and lower support members 164, 166 may have a body corresponding in size and shape to any multi-petal seal member, e.g., the multi-petal seal member 162. The openings 163, 165 are sized to allow proper coverage of the multi-petal seal member 162 while still allowing larger surgical instruments (not shown) to be received through the seal assembly 160 within minimal effect on forces. In embodiments, the openings 163, 165 may range from about 0.300 to about 0.450" in diameter.

The upper and lower support members 164, 166 may be formed of polyisoprene, liquid silicone rubber, or any other material with sufficient stretching properties. In embodiments, the upper and lower support members 164, 166 measure between 0.006" and 0.015" thick. As will be described in further detail below, the upper and lower support members 164, 166 form a sandwich around the multi-petal seal member 162 to lessen the impact of leak paths within the multi-petal seal member 162.

Figure 7:
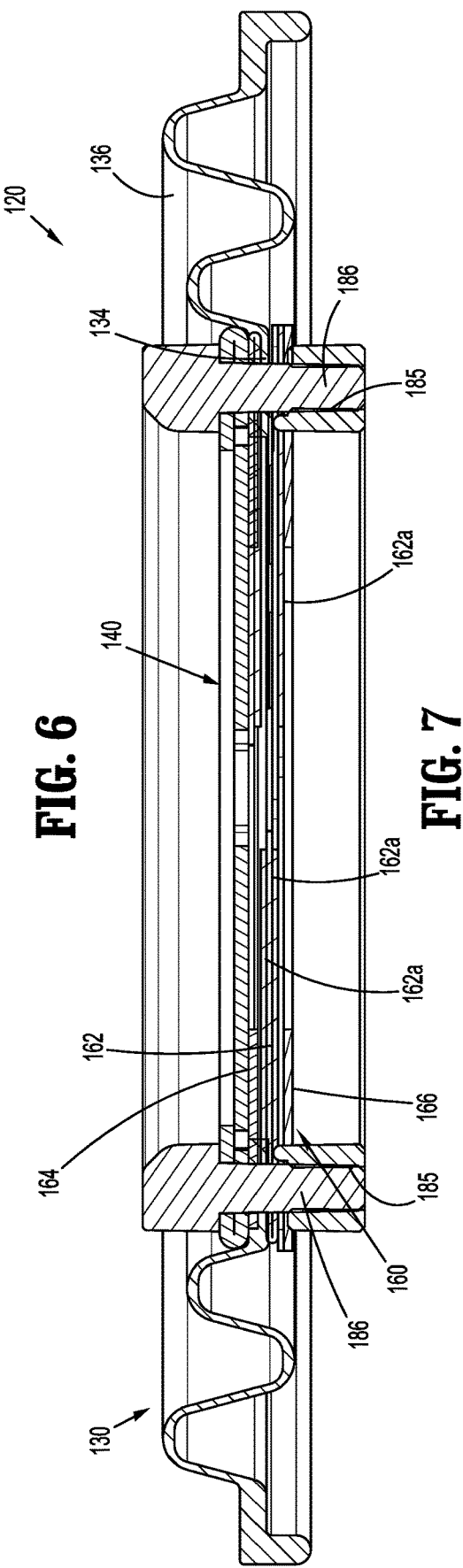
FIG. 7 is a side cross-sectional view of the seal assembly shown in FIG. 4 taken along section line 7-7.
Figure 8:
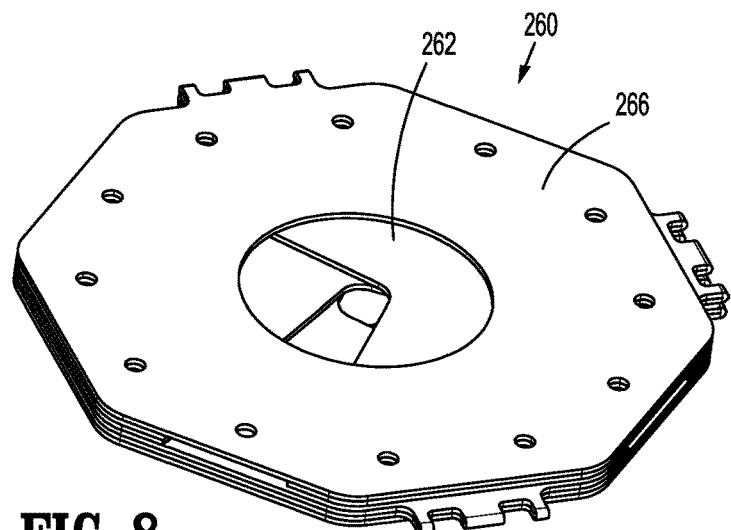
FIG. 8 is a perspective view of a seal assembly according to another embodiment of the present disclosure.

With particular reference to FIG. 7, the overlapping layers of the multiple petals of the multi-petal seal member 162 of the seal assembly 160 may provide pathways for insufflation fluid to leak through the valve assembly 120. The upper and lower support members 164, 166 of the seal assembly 160 are configured reduce the potential for leakage of insufflation fluid through the multi-petal seal member 162. More particularly, the upper and lower support members 164, 166 are disposed on respective proximal and distal sides of the multi-petal seal member 162 and are configured to be compressed about the multi-petal seal member 162. By compressing the multi-petal seal member 162 between the upper and lower support members 164, 166, leakage between the layers of the multi-petal seal member 162 may be greatly reduced and/or eliminated. The upper and lower support members 164, 166 may also assist in preventing or reducing damage to the multi-petal seal member 162 during insertion, manipulation, and removal of a surgical instrument therethrough.

Each of the multi-petal seal member 162, the upper support member 164, and the lower support member 166 defines a plurality of openings 161a, 163a, 165a, respectively, for receiving legs 186 extending from the upper retainer member 182 of the retainer assembly 180.

With continued reference to FIG. 7, the upper support member 164 of the seal assembly 160 is disposed between the guard assembly 140 and the inner annular ring 134 of the centering mechanism 130. The multi-petal seal member 162 is disposed on the opposite side of the inner annular ring 134 and the lower support member 164 of the seal assembly 160 is disposed adjacent the multi-petal seal member 162. The plurality of legs 186 of the retainer assembly 180 are received through each of the centering mechanism 130, the guard assembly 140, and the seal assembly 160, including the multi-petal seal 162 and the upper and lower support members 164, 166.

The upper and lower retainer members 182, 184 of the retainer assembly 180 are configured to squeeze the upper and lower support members 164, 166 with the seal assembly 160 sandwiched between. In this manner, any leaks existing between the petals 162a of the multi-petal seal member 162 are reduced in size or eliminated.

The retainer assembly 180 (FIG. 3) of the valve assembly 120 is configured to secure the guard assembly 140 relative to the seal assembly 160, and secure the guard and seal assemblies 140, 160 to the centering mechanism 130. The retainer assembly 180 includes the upper retainer member 182, and a lower retainer member 184. As noted above, the upper retainer member 182 includes a plurality of pins 186. The plurality of pins 186 extend from a bottom surface of the upper retainer member 182. Each pin of the plurality of pins 186 is configured to be lockingly received within an opening of a plurality of openings 185 (FIG. 3) lower retainer member 184. In embodiments, the plurality of pins 186 is welded, glued, adhered, bonded or otherwise secured within the plurality of openings 185 in the lower retainer member 184 to secure the upper retainer member 182 and the lower retainer member 184 together. Alternatively, the lower retainer member 184 may instead, or additionally, include a plurality of pins (not shown) with the upper retainer member 182 defining a plurality corresponding openings (not shown). Either or both of the upper and lower retainer members 182, 184 may include locking features (not shown) for engaging the plurality of pins and securing the upper retainer member 182 to the lower retainer member 184.

The plurality of pins 186 of the upper retainer member 182 extend through the ring portion 142 of the guard assembly 140, through the openings 163a, 165a, 167a in the respective multi-petal seal member 162, and upper and lower support members 164, 166 of the seal assembly 160, through the inner annular ring 134 of the centering mechanism 130, and into the openings 185 in the lower retainer member 184.

During a surgical procedure utilizing cannula assembly 100, a surgical instrument (not shown) is introduced into the instrument valve housing 110 through the longitudinal passage 113 in the upper, lower, and inner housing sections 112, 114, 116. As described above, the distal end of the surgical instrument engages the guard assembly 140 causing flap portions of the guard assembly 140 to flex downward into contact with multi-petal seal member 162 of the seal assembly 160 to cause the central opening 163 of the multi-petal seal member 162 to open to accommodate passage of the surgical instrument through the seal assembly 160. By compressing the upper and lower support members 164, 166 of the seal assembly 160 about the multi-petal seal member 162 in a sandwich-like manner, leaks through the multi-petal seal member 162 are reduced and/or eliminated.

With reference now to FIGS. 8-15, a seal assembly according to another embodiment of the present disclosure is shown generally as seal assembly 260. The seal assembly 260 is interchangeable with the seal assembly 160 described herein above, and will only be described in detail as relates to the differences therebetween.

Figure 9:
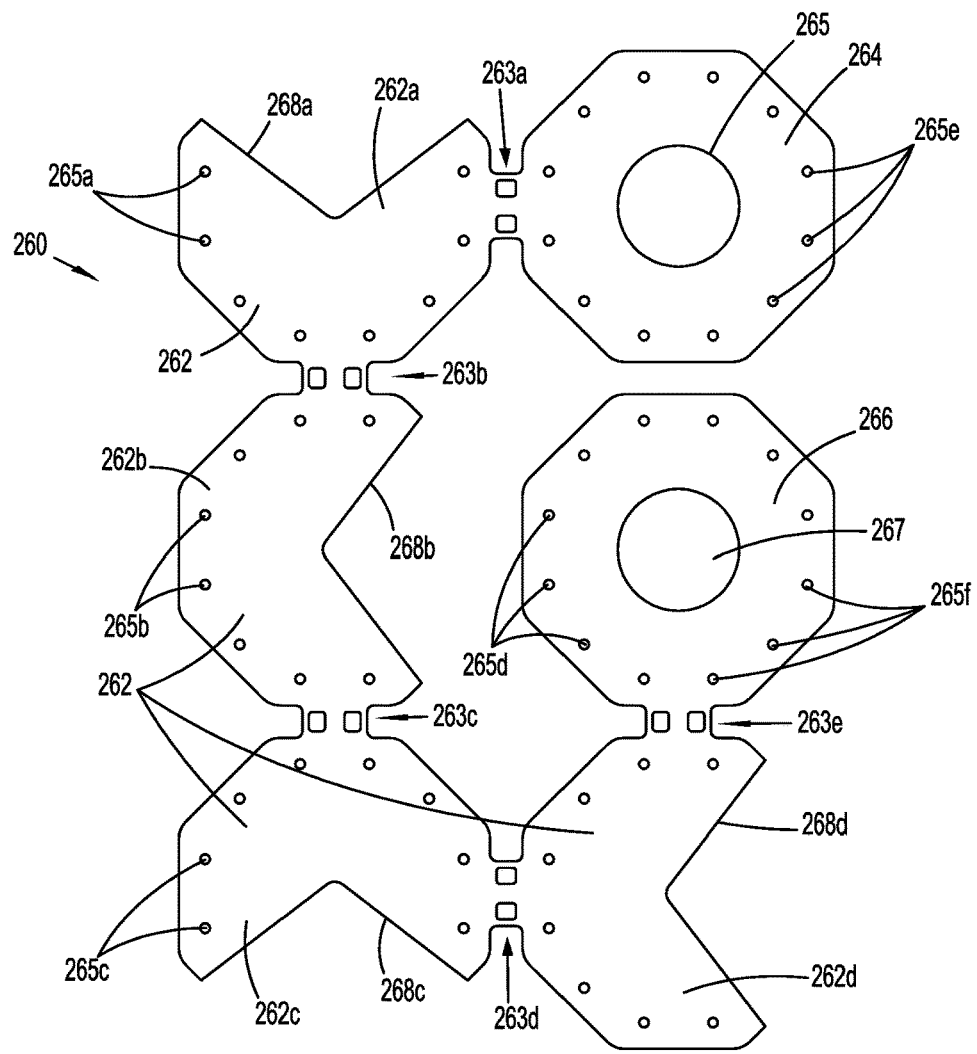
FIG. 9 is a top view of the seal assembly shown in FIG. 8, in an unfolded condition.

With particular reference to FIG. 9, the seal assembly 260 includes a plurality of seal sections 262, an upper support member 264, and a lower support member 266. The plurality of seal sections 262 and the upper and lower support members 264, 266 are secured to one other. In embodiments, and as shown, the seal assembly 260 is integrally formed, i.e., one-piece or monolithic. The seal assembly 260 may be stamped, molded, or otherwise formed.

The plurality of seal sections 262 of the seal assembly 260 includes first, second, third, and fourth sections 262a, 262b, 262c, 262d. Although shown with only four (4) sections, it is envisioned that the seal assembly 260 may include as many as eight (8) sections. The plurality of seal sections 262 and the upper and lower support members 264, 266 of seal assembly 260 may be formed of the same or different material. In embodiments, at least the plurality of seal sections 262 are formed of an elastic material, e.g., rubber, polyisoprenes, or silicone elastomers. In embodiments, the first, second, third, and fourth sections 262a, 262b, 262c, 262d may include one or more fabric layers.

Each of the first, second, third, and fourth sections 262a, 262b, 262c, 262d of the multi-petal seal member 262 of the seal assembly 260 and the upper and lower support members 264, 266 include an octagonal shape, although other shapes are envisioned. An inner edge 268a, 268b, 268c, 268d of the respective first, second, third, and fourth sections 262a, 262b, 262c, 262d of the seal assembly 260 may be straight (not shown), or, as shown, may define a V-shape or cutaway. In embodiments, the V-shape defines an angle between forty-five degrees (45°) and one-hundred eighty degrees (180°). In embodiments, the V-shape defines an angle of ninety degrees (90°). The V-shape of the inner edges 268a, 268b, 268c, 268d of the respective first, second, third, and fourth sections 262a, 262b, 262c, 262d of the seal assembly 260 facilitates reception of a surgical instrument (not shown) through the seal assembly 260. The first, second, third, and fourth sections 262a, 262b, 262c, 262d of the multi-petal seal member 262 may form a flat seal (as shown), or may form a conical seal.

With continued reference to FIG. 9, the upper support member 264 and the first section 262a of the seal assembly 260 are connected to one another by a connector portion 263a, the first and second sections 262a, 262b of the seal assembly 260 are connected to one another by a connector portion 263b, the second and third sections 262b, 262c of the seal assembly 260 are connected to one another by a connector portion 263c, the third and fourth sections 262c of the seal assembly 260 are connected to one another by a connector portion 263d, the fourth sections 262d and the lower support member 266 of the seal assembly 260 are connected to one another by a connector portion 263e. In embodiments, the connector portions 263a, 263b, 263c, 263d, 263e of the seal assembly 260 include a living hinge, or are otherwise formed to facilitate folding of the sections and the support members.

Each of the first, second, third, and fourth sections 262a, 262b, 262c, 262d and the upper and lower support members 264, 266 define a plurality of openings 265a, 265b, 265c, 265d along an outer perimeter of each section 262a, 262b, 262c, 262d, respectively, and a plurality of openings 265e, 265f along an outer perimeter of the respective upper and lower support members 244, 246. The plurality of openings 265a, 265b, 265c, 265d, 265e, 265f are configured to receive pins 186 (FIG. 7) of the retainer assembly 180 to maintain the seal assembly 260 in the folded condition and to secure the seal assembly 260 relative to the guard assembly 140 and the centering mechanism 130.

Figure 10:
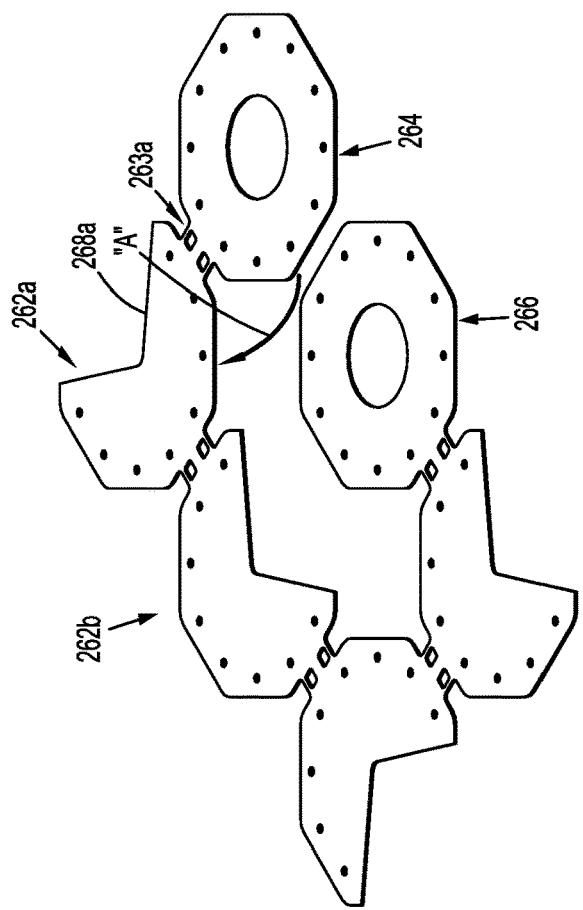

The method of folding the seal assembly 260 will now be described with reference to FIGS. 10-15. Referring initially to FIG. 10, the upper support member 264 is folded relative to the first section 262a of the plurality of seal section 262 at the connector portion 263a between the upper support member 264 and the first section 262a, as indicated by arrow "A", such that the upper support member 264 overlaps the first section 262a. In this manner, the plurality of openings 265e aligns with the plurality of openings 265a in the overlapping portion of the first section 262a of the seal assembly 260.

Figure 11:
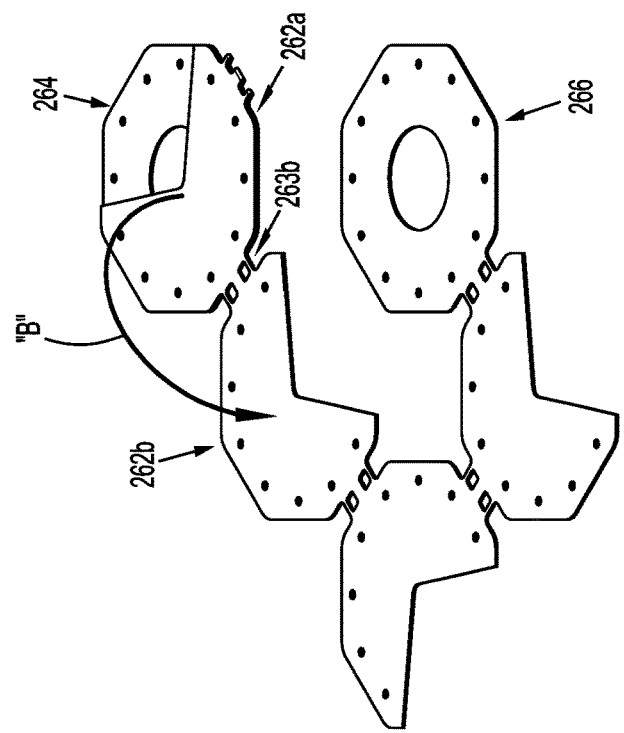
FIGS. 10-14 are perspective views of the seal assembly shown in FIG. 8, in sequential partially folded conditions.

Turning to FIG. 11, the first section 262a of the seal assembly 260 is folded relative to the second section 262a of the seal assembly 260 at the connector portion 263b between the first and second sections 262a, 262b, as indicated by arrow "B", such the first section 262a overlaps the second section 262b of the seal assembly 260. In this manner, the plurality of openings 265a of the first section 262a aligns with the plurality of openings 265b in the overlapping portion of the second section 262b of the seal assembly 260.

Figure 12:
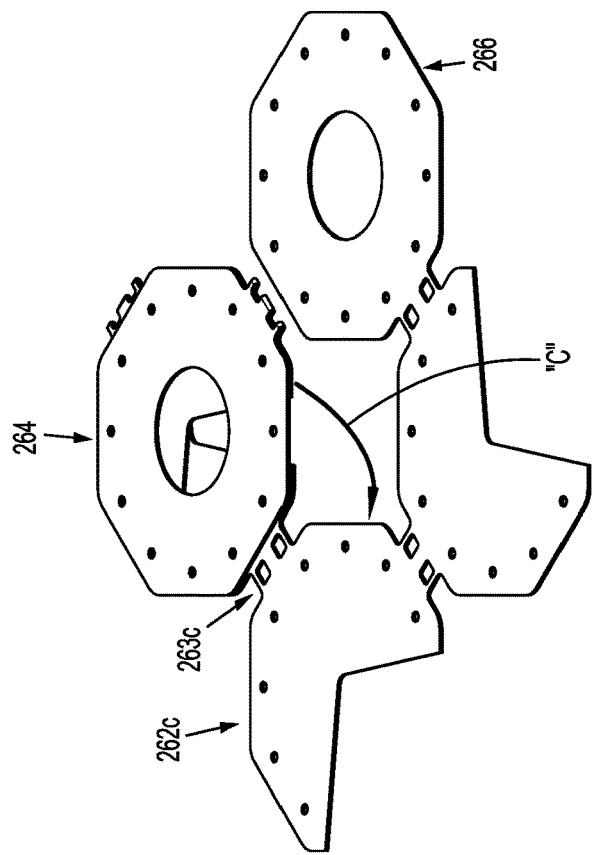
Figure 15:
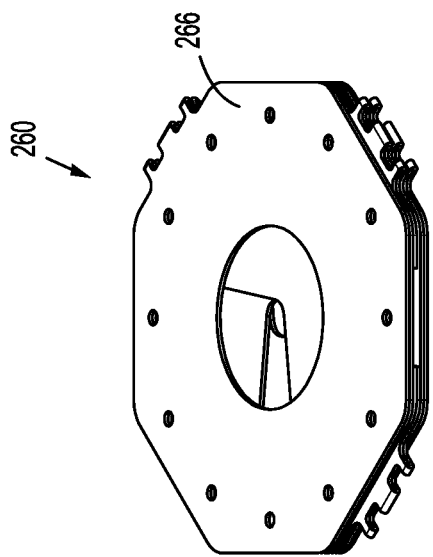
FIG. 15 is a perspective view of the seal assembly shown in FIG. 8, in a fully folded condition.

With reference to FIG. 12, the second section 262a of the seal assembly 260 is folded relative to the third section 262b at the connector portion 263c between the second and third sections 262a, 262b, as indicated by arrow "C", such that the second section 262b overlaps the third section 262c of the seal assembly 260. In this manner, the plurality of openings 265b of the second section 262b aligns with the plurality of openings 265c in the overlapping portion of the third section 262c of the seal assembly 260.

Figure 13:
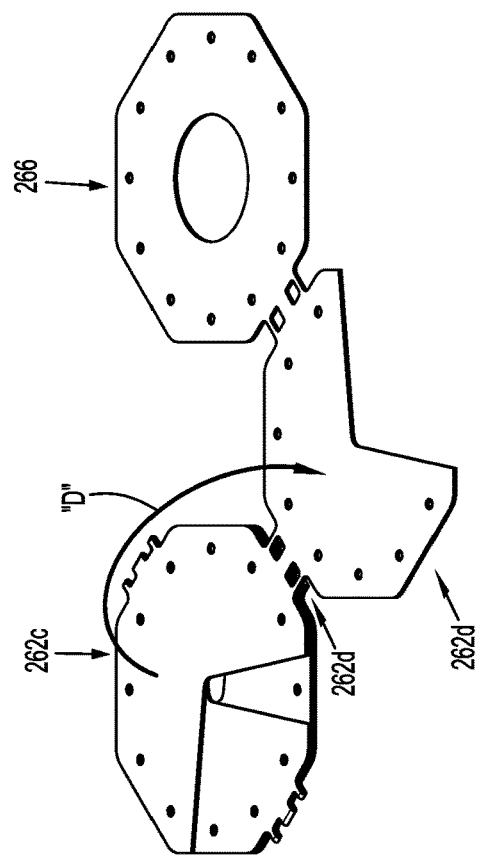

Referring to FIG. 13, the third section 262c of the seal assembly 260 is folded relative to the fourth section 262d of the seal assembly 260 at the connector portion 263d between the third and fourth sections 262c, 262d, as indicated by arrow "D", such that the third section 262c overlaps the fourth section 262d of the seal assembly 260. In this manner, the plurality of openings 265c of the third section 262c aligns with the plurality of openings 265d in the overlapping portion of the fourth section 168 of the seal assembly 160.

Figure 14:
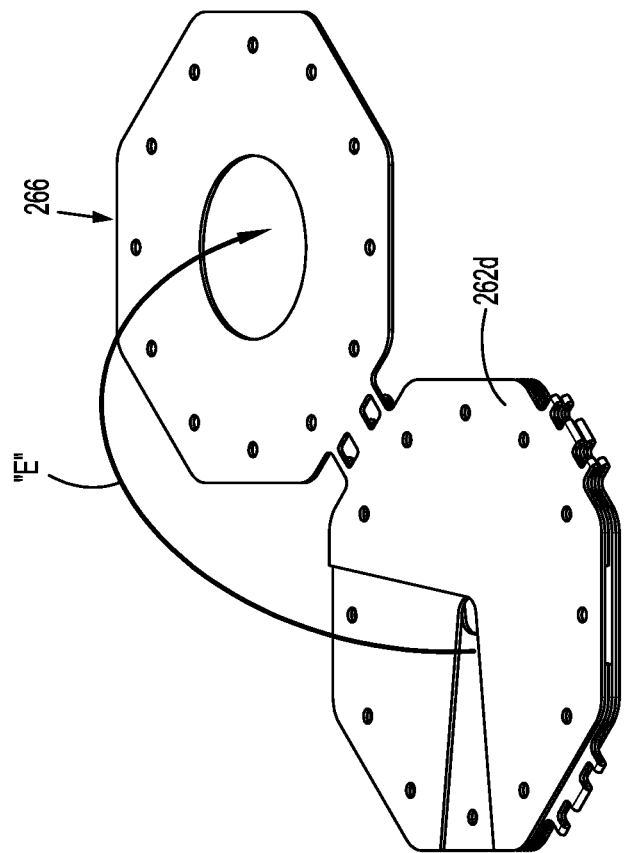

With reference to FIG. 14, the fourth section 262d of the seal assembly 260 is folded relative to the lower support member 266 of the seal assembly 260 at the connector portion 163e between the fourth section 262d and the lower support member 266, as indicated by arrow "E", such that the fourth section 262d overlaps the lower support member 266. In this manner, the plurality of openings 265d of the fourth section 262d aligns with the plurality of openings 265f in the overlapping portion of the lower support member 266.

The seal assembly 260 is secured within the instrument valve housing 110 (FIG. 2) in a similar manner to seal assembly 160 described hereinabove. The seal assembly 260 operates in a similar manner to seal assembly 160.

While various embodiments of the present disclosure have been shown and described herein, it will be obvious to those skilled in the art that these embodiments are provided by way of example only. Numerous variations, changes, and substitutions will now occur to those skilled in the art without departing from the present disclosure. Accordingly, it is intended that the invention be limited only by the spirit and scope of the appended claims.

What is claimed is:

1. A surgical access assembly comprising:
   an instrument valve housing including upper, lower, and inner housing sections and defining a cavity;
   a cannula assembly extending distally from the instrument valve housing; and
   a valve assembly disposed within the cavity of the instrument valve housing, the valve assembly including:
   a guard assembly including a plurality of guard sections,
   a seal assembly disposed adjacent to and entirely distal of the guard assembly, the seal assembly including a plurality of seal sections and upper and lower support members, the plurality of seal sections being movable from an unfolded configuration to folded configuration in which the seal assembly forms a seal member defining an opening to facilitate sealed passage of a surgical instrument, the upper and lower support members being disposed on respective proximal and distal sides of the plurality of seal sections and being compressed about the plurality of seal sections to sandwich the plurality of seal sections therebetween;
   a centering mechanism for maintaining the seal assembly and guard assembly centered within the cavity of the instrument valve housing; and
   a retainer assembly for supporting the guard assembly and the seal assembly relative to the centering mechanism, the retainer assembly including first and second retainer members and a plurality of pins extending between the first and second retainer members.

2. The surgical access assembly of claim 1, wherein the upper and lower support members define an opening from about 0.30" to about 0.45".

3. The surgical access assembly of claim 1, wherein the upper and lower support members measure from about 0.006" to about 0.015" in thickness.

4. The surgical access assembly of claim 1, wherein the plurality of seal sections is formed of polyisoprene or liquid silicone rubber.

5. The surgical access assembly of claim 1, wherein each seal section of the plurality of seal sections is connected to an adjacent seal section of the plurality of seal sections by a connector portion.

6. The surgical access assembly of claim 5, wherein the connector portions include living hinges.

7. The surgical access assembly of claim 1, wherein the upper support member is connected to a seal section of the plurality of seal sections by a connector portion and the lower support member is connected to another seal section of the plurality of seal sections by another connector portion.

8. The surgical access assembly of claim 1, wherein an inner edge of each seal section of the plurality of seal sections defines a V-shape.

9. The surgical access assembly of claim 8, wherein the V-shape includes an angle from about one hundred eighty degrees to about two hundred seventy-five degrees.

10. The surgical access assembly of claim 1, wherein the plurality of seal sections includes first, second, third, and fourth seal sections, each of the first, second, third, and fourth seal sections overlapping the adjacent second, third, fourth, and first seal sections.

11. The surgical access assembly of claim 1, wherein the plurality of pins are received through the guard assembly and the seal assembly for retaining the guard and seal assemblies relative to each other.

12. The surgical access assembly of claim 1, wherein the centering mechanism includes a bellows.

13. The surgical access assembly of claim 1, wherein the upper and lower support members include a hexagonal shape.

14. The surgical access assembly of claim 1, wherein the upper and lower support members include an octagonal shape.

15. A valve assembly comprising:
   a guard assembly including a plurality of guard sections,
   a seal assembly disposed adjacent to and entirely distal of the guard assembly, the seal assembly including a plurality of seal sections and upper and lower support members, the plurality of seal sections being movable from an unfolded configuration to folded configuration in which the seal assembly forms a seal member defining an opening to facilitate sealed passage of a surgical instrument, the upper and lower support members being disposed on respective proximal and distal sides of the plurality of seal sections and being compressed about the plurality of seal sections to sandwich the plurality of seal sections therebetween;
   a centering mechanism for maintaining the seal assembly and guard assembly centered within a cavity of a surgical access assembly; and
   a retainer assembly for supporting the guard assembly and the seal assembly relative to the centering mechanism, the retainer assembly including upper and lower retainer members and a plurality of pins extending between the upper and lower retainer members.

16. The valve access assembly of claim 15, wherein the plurality of pins are received through the guard assembly and the seal assembly for retaining the guard and seal assemblies relative to each other.

17. The valve access assembly of claim 15, wherein the upper support member is connected to a seal section of the plurality of seal sections by a connector portion and the lower support member is connected to another seal section of the plurality of seal sections by another connector portion.

18. A surgical access assembly comprising:
   an instrument valve housing including upper, lower, and inner housing sections and defining a cavity;
   a cannula assembly extending distally from the instrument valve housing; and
   a valve assembly disposed within the cavity of the instrument valve housing, the valve assembly including:
      a guard assembly including a plurality of guard sections;
      a seal assembly disposed adjacent to and distal of the guard assembly, the seal assembly including a plurality of seal sections and upper and lower support members, each seal section of the plurality of seal sections being connected to an adjacent seal section of the plurality of seal sections by a living hinge, the plurality of seal sections being movable from an unfolded configuration to folded configuration in which the seal assembly forms a seal member defining an opening to facilitate sealed passage of a surgical instrument, the upper and lower support members being disposed on respective proximal and distal sides of the plurality of seal sections and being compressed about the plurality of seal sections to sandwich the plurality of seal sections therebetween;
      a centering mechanism for maintaining the seal assembly and guard assembly centered within the cavity of the instrument valve housing; and
      a retainer assembly for supporting the guard assembly and the seal assembly relative to the centering mechanism, the retainer assembly including first and second retainer members and a plurality of pins extending between the first and second retainer members.

19. The surgical access assembly of claim 18, wherein the upper support member is connected to a seal section of the plurality of seal sections by a connector portion and the lower support member is connected to another seal section of the plurality of seal sections by another connector portion.

* * * * *